(12) United States Patent
Ho

(10) Patent No.: US 11,406,841 B2
(45) Date of Patent: Aug. 9, 2022

(54) MAGNETIC STIMULATION WITH VARIABLE PULSED INTERVALS

(71) Applicant: Conway Ho, La Palma, CA (US)

(72) Inventor: Conway Ho, La Palma, CA (US)

(*) Notice: Subject to any disclaimer, the term of this patent is extended or adjusted under 35 U.S.C. 154(b) by 332 days.

(21) Appl. No.: 16/365,676

(22) Filed: Mar. 27, 2019

(65) Prior Publication Data

US 2019/0308029 A1 Oct. 10, 2019

Related U.S. Application Data

(60) Provisional application No. 62/654,476, filed on Apr. 8, 2018.

(51) Int. Cl.
*A61N 2/00* (2006.01)
*A61B 5/00* (2006.01)
*A61N 2/02* (2006.01)
*A61B 5/30* (2021.01)
*A61B 5/369* (2021.01)

(52) U.S. Cl.
CPC ............. *A61N 2/006* (2013.01); *A61B 5/30* (2021.01); *A61B 5/369* (2021.01); *A61B 5/726* (2013.01); *A61N 2/02* (2013.01)

(58) Field of Classification Search
CPC ...... A61N 2/006; A61N 2/02; A61B 5/04004; A61B 5/0476; A61B 5/4836; A61B 5/165; A61B 5/726; A61B 5/0482
See application file for complete search history.

(56) References Cited

U.S. PATENT DOCUMENTS

| | | | |
|---|---|---|---|
| 6,488,617 B1 * | 12/2002 | Katz | A61B 5/0482 600/26 |
| 9,308,385 B2 | 4/2016 | Jin | |
| 2009/0082690 A1 | 3/2009 | Phillips et al. | |
| 2019/0082990 A1 * | 3/2019 | Poltorak | A61B 5/0476 |

* cited by examiner

*Primary Examiner* — Christine H Matthews
*Assistant Examiner* — Joshua Daryl D Lannu

(57) ABSTRACT

A method of modulating a brain activity of a mammal is achieved by subjecting the mammal to repetitive transcranial magnetic stimulation (rTMS) with an rTMS apparatus at variable pulse intervals for a time sufficient to modulate said brain activity. Improvement in a physiological condition or a clinical condition is achieved. Conditions to be treated include but are not limited to PTSD, autism spectrum disorder and Alzheimer's disease. Wavelet transform analysis is used to determine the variable pulse intervals employed.

6 Claims, 1 Drawing Sheet

MAGNETIC STIMULATION WITH VARIABLE PULSED INTERVALS

The present application claims priority under 35 U.S.C. 119(e) to U.S. Provisional Application No. 62/654,476, filed on Apr. 8, 2018, the disclosure of which is incorporated herein by reference in its entirety.

FIELD OF THE INVENTION

The present invention relates to methods of modulating brain activity with repetitive transcranial magnetic stimulation (rTMS) wherein the rTMS is administered with variable pulse intervals for a time sufficient to modulate said brain activity wherein an improvement in a physiological condition or a clinical condition is achieved. The variable pulse interval settings are derived from a patient's EEG signal that has been extracted from analysis with a wavelet transform.

BACKGROUND OF THE INVENTION

Transcranial magnetic stimulation and rTMS have been used to treat many psychological and medical disorders such as major depressive disorder, Parkinson's disease, PTSD, Alzheimer's disease, autism spectrum disorder (ASD), schizophrenia, pain management and others. Recently, Jin and Phillips, in US Patent Publication 2009/0082690, have disclosed a treatment protocol using rTMS where the output of the magnetic field is adjusted based on a patient's EEG intrinsic frequencies in an attempt to alter the patient's intrinsic EEG frequencies. U.S. Pat. No. 9,308,385 uses a different approach to administer rTMS by using a frequency based on a biological metric or an harmonic of a biological metric.

rTMS is delivered by an apparatus that is comprised of magnetic coils that provide pulsed magnetic fields. The frequencies and intensity can be varied if desired. Prior to the present invention rTMS treatments have consisted of the delivery of a single frequency at a set intensity. The present invention provides a novel rTMS delivery system that delivers rTMS with variable pulse intervals with multiple frequencies and variable output intensities.

SUMMARY OF THE INVENTION

Briefly, in accordance with the present invention, the brain activity of a mammal is modulated by subjecting the mammal to repetitive transcranial magnetic stimulation (rTMS) with variable pulse intervals determined by individual EEG characteristics for a time sufficient to modulate said brain activity wherein an improvement in a physiological condition or a clinical condition is achieved. In one embodiment, the variable pulse intervals are determined by subjecting the mammal to an EEG to create an EEG data set and analyzing the EEG data set with a wavelet transform algorithm. The wavelet transform algorithm identifies a unique EEG signal pattern for the mammal/patient. The EEG signal pattern is then used to generate a sequence of TTL (transistor-transistor logic) or other triggering pulses to program the rTMS apparatus to provide variable pulse intervals and variable intensities. Brain activity to be modulated can be any one or more desired frequency bandwidth(s) and includes the brain frequency bandwidth of 3-7 Hz, the brain frequency bandwidth of 8-13 Hz, the brain frequency bandwidth of 15-20 Hz, and the brain frequency bandwidth of 35-45 Hz and any sub-bandwidth group within those ranges. If a frequency bandwidth between 8-13 Hz is targeted to treat a patient, the actual bandwidth used to treat that patient can be narrowed within that bandwidth range depending on the variation of patient's EEG oscillation intervals, such as, for example, 105 ms-110 ms, ie a frequency bandwidth between 9.1-9.5 Hz. Success in the modulation is achieved when the targeted frequency bandwidth has an increase in amplitude or relative power density in addition to improvement in symptoms associated with the clinical and physiological conditions being treated.

Physiological conditions and medical conditions that can be improved by modulating the brain activity according to the present invention are any conditions where abnormal brain activity contributes to a specific condition. Improvements are seen when the amplitude of the desired or targeted brain wave bands acquire an increase in amplitude or relative power density. Conditions that are treated include but are not limited to autism spectrum disorder (ASD), Alzheimer's Disease (AD), Post Traumatic Stress Disorder (PTSD), Traumatic Brain Injury (TBI), memory impairment, depression, pain, addiction, Obsessive Compulsive disorders (OCD), anxiety, Parkinson's disease, hypertension, libido dysfunction, motor function abnormalities, small height in young children, stress, obesity, sleep disorders, eating disorders, concentration/focus abnormalities, speech abnormalities, intelligence deficits, cognition abnormalities, Attention Deficit Hyperactivity Disorders (ADHD), schizophrenia, coma, bipolar disorders, tinnitus, fibromyalgia, chronic Lyme disease, Rheumatoid arthritis and other autoimmune diseases, gout, diabetes, arthritis, trauma rehab, athletic performance, cognitive improvement, and stroke.

Of particular interest in practicing the present invention, a patient is subjected to repetitive transcranial magnetic stimulation (rTMS) with variable pulse intervals for a time sufficient to modulate a brain activity in the patient where an improvement in a physiological condition or a clinical condition is achieved. The patient is subjected to an EEG to create an EEG data set. The EEG data set is analyzed with a wavelet transform. The extracted signal by wavelet transform analysis is then used to program the variable pulse intervals (frequencies and amplitudes) into the rTMS apparatus. The wavelet transform algorithm extracts a unique EEG signal and variable pulse interval profile that results in the desired improvements in the physiological or medical condition that is being treated.

DETAILED DESCRIPTION OF THE INVENTION

Figure 1:
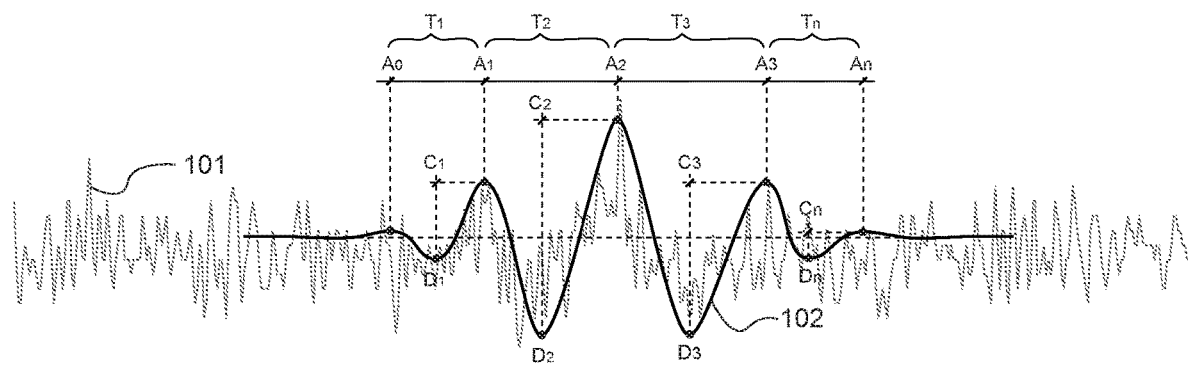
FIG. 1 shows EEG raw data and extracted signal by a wavelet analysis.

The term "mammal" when used herein includes any mammal but especially humans. Non-human mammals include non-human primates, zoo animals, companion animals (dogs, cats) and performance animals such as race horses and breeding animals. Any reference to "humans" described herein will have applicability to other mammals that exhibit the same physiological or medical conditions. Any reference to "patient" when used herein has applicability to any mammal (preferably humans) that may experience the particular condition to which the patient reference is made.

In practicing the present invention, an EEG is conducted on a patient experiencing physiological conditions and/or medical conditions in need of treatment. The raw EEG data is analyzed with a wavelet transform algorithm resulting in a unique patient EEG wavelet signal. The pattern of the EEG wavelet signal is used to program the TTL pulses, or other triggers, generated by the rTMS apparatus into variable pulse intervals. rTMS is administered to the patient with variable pulse intervals for a time sufficient to modulate a brain activity which results in an improvement in the physiological condition or the clinical condition being treated. In a preferred embodiment variable pulse intervals are employed in an rTMS protocol used for a time sufficient to modulate a brain activity resulting in an improvement in a physiological condition or a clinical condition. Preferably, the treatments are administered daily or 5 days/week for a month after which the patient's progress will be re-evaluated. The variable pulse interval settings are achieved by programming the rTMS apparatus with the patient's EEG signal extracted by wavelet analysis to provide magnetic stimulation with variable pulse intervals. The specific brain activity, or brain wave frequency bandwidth, to be modulated is dictated by the patient's EEG. A preferred brain frequency bandwidth is 8-13 Hz. The maximum intensity setting of the magnetic pulses is generally limited to the patient's motor threshold or lower. It is preferred to set the peak pulse power/intensity of the rTMS to about 80% of the patient's motor threshold.

The rTMS treatments according to the present invention are administered according to well known protocols employing magnetic coils. The time of actual magnetic stimulation over a set period of time will vary based on each clinical presentation. It is preferred to administer the magnetic stimulation for six continuous seconds per minute of the rTMS session. Sessions can last from 15 to 60 minutes and preferably about 30 minutes. Magnetic coils are placed in close proximity or against a patient's head preferably adjacent to the area of the head where the desired brain frequency wavelengths predominate in the patient's brain. For example, if treating a patient with a frequency bandwidth in the 8-13 Hz range then the magnetic rTMS coils are generally placed against the frontal lobe area (forehead) of the patient where the variable pulse interval frequencies are administered. For treating a patient with variable pulse interval frequencies in more than one frequency bandwidth range, the magnetic coils are positioned adjacent to brain regions that the patient's EEG has identified as having poor coherence, low energy and/or regions that are non-synchronous.

Patients/mammals can be treated for any one or more of the brain wave frequency ranges described herein. When more than one brain wave frequency bandwidth range is targeted the rTMS variable pulsed intervals can be administered simultaneously or sequentially in one treatment session. When treating multiple brain wave frequency bandwidth ranges, the rTMS can be delivered by an rTMS device that can deliver variable pulsed interval frequencies to more than one area of the patient's head. Alternatively, multiple rTMS devices can be used to deliver the desired variable pulsed interval frequencies to the desired areas.

A patient in need of treatment is subjected to an EEG resulting in an EEG data set. The EEG data is then analyzed with a wavelet transform algorithm resulting in the patient's EEG signal pattern 102 (FIG. 1). The patient's EEG signal extracted by wavelet analysis is then used to determine the variable pulse intervals used in the patient's rTMS treatment.

Referring to FIG. 1, the EEG raw data profile 101 is analyzed with a wavelet transform algorithm resulting in the patient's individual wavelet pattern 102. The EEG signal pattern is then analyzed to determine a time sequence with period variation $A_0, A_1, A_2 \ldots A_n$ and amplitude settings with intensity variation $C_1$-$D_1$, $C_2$-$D_2$, $C_3$-$D_3 \ldots C_n$-$D_n$. The power settings are determined by the magnitude of each EEG wave measured between the peak (C) and the prior trough (D). The rTMS trigger pulse occurs at the peak of each wave determined by the wavelet analysis, and in FIG. 1, that would involve "n" number of pulses—one pulse at $A_1, A_2, \ldots A_n$. It should be understood that n>1 and there could be more or less than 3 pulses per train of pulses depending on the EEG and wavelet data. The timing of the pulses is shown by the T values $T_1$, $T_2$, and $T_n$ which are determined by the period between EEG waves depicted by the wavelet transform analysis. When targeting brain waves in the 8-13 Hz range the timing of the pulses will vary but will be between 75-125 milliseconds (ms).

Figure 2:
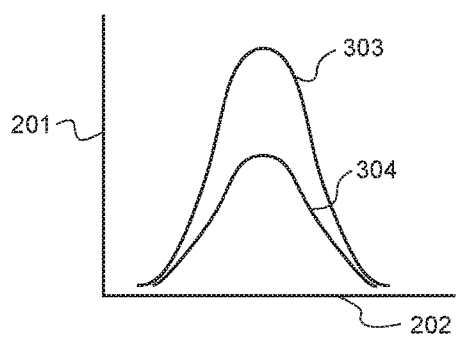
FIG. 2 shows the results of a patient's EEG power spectra before and after treatment.

FIG. 2 is a graph of power spectra of a patient's EEG and plots power 201 against frequency 202 showing pre-treatment 304 and a post-treatment 303 profiles.

Once a patient's EEG signal is identified by wavelet transform analysis it is used to program the rTMS apparatus to deliver the variable pulse interval settings to be used in that patient's rTMS treatment.

Additionally, the present invention relates to an improved rTMS apparatus wherein the improvement comprises a means for delivering rTMS pulses as variable pulse intervals. In one embodiment, the rTMS apparatus is programmed to deliver variable pulse intervals. Preferably the peak power or intensity delivered to a patient is below the patient's motor threshold and preferably at 40-90% of the patient's motor threshold while the rest of the pulse intensity varies proportional to the corresponding EEG signal wave amplitude.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A method of modulating a brain activity of a mammal which comprises subjecting the mammal to repetitive transcranial magnetic stimulation (rTMS) with variable pulse intervals to modulate said brain activity wherein the variable pulse intervals are derived from an EEG signal of the mammal that is extracted by wavelet analysis.

2. The method of claim 1 wherein the brain activity being modulated comprises one or more brain wave frequency bandwidths between 3 and 7 Hz, 8 and 13 Hz, 15 and 20 Hz and 35 and 45 Hz.

3. The method of claim 2 wherein the brain activity being modulated is a brain wave band between 8 and 13 Hz.

4. A method of treating PTSD in a human patient which comprises:
   a. subjecting the patient to an EEG to create an EEG data set,
   b. analyzing the EEG data set with a wavelet transform resulting in an EEG signal pattern,
   c. using the EEG signal pattern to program a repetitive transcranial magnetic stimulation (rTMS) apparatus to deliver electromagnetic pulses having variable pulse intervals and d. subjecting the patient to repetitive transcranial magnetic stimulation (rTMS) from said programmed repetitive transcranial magnetic stimulation (rTMS) apparatus, wherein said rTMS apparatus delivers electromagnetic pulses having variable pulse intervals derived from the EEG signal pattern.

5. A method of treating autism spectrum disorder (ASD) in a human patient which comprises:
   a. subjecting the patient to an EEG to create an EEG data set,
   b. analyzing the EEG data set with an EEG signal transform resulting in an EEG signal pattern,
   c. using the EEG signal pattern to program a repetitive transcranial magnetic stimulation (rTMS) apparatus to deliver electromagnetic pulses having variable pulse intervals and
   d. subjecting the patient to repetitive transcranial magnetic stimulation (rTMS) from said programmed repetitive transcranial magnetic stimulation (rTMS) apparatus, wherein the rTMS apparatus delivers electromagnetic pulses having variable pulse intervals derived from the EEG signal pattern.

6. A method of treating Alzheimer's disease in a human patient which comprises:
   a. subjecting the patient to an EEG to create an EEG data set,
   b. analyzing the EEG data set with an EEG signal transform resulting in an EEG signal pattern,
   c. using the EEG signal pattern to program a repetitive transcranial magnetic stimulation (rTMS) apparatus to deliver electromagnetic pulses having variable pulse intervals, and
   d. subjecting the patient to repetitive transcranial magnetic stimulation (rTMS) from said programmed repetitive transcranial magnetic stimulation (rTMS) apparatus, wherein said rTMS apparatus delivers electromagnetic pulses having variable pulse intervals derived from the EEG signal pattern.

* * * * *